(12) United States Patent
Mantovani et al.

(10) Patent No.: US 10,335,135 B2
(45) Date of Patent: Jul. 2, 2019

(54) FIXING DEVICE FOR SUTURE THREADS TO BE INSERTED INTO A BONE TISSUE

(75) Inventors: Matteo Mantovani, Reggio Emilia (IT); Enrico Rasia Dani, Torri di Quartesolo (IT)

(73) Assignee: NCS LAB S.R.L., Carpi (IT)

( * ) Notice: Subject to any disclaimer, the term of this patent is extended or adjusted under 35 U.S.C. 154(b) by 364 days.

(21) Appl. No.: 13/879,764

(22) PCT Filed: Oct. 13, 2011

(86) PCT No.: PCT/IB2011/054536
§ 371 (c)(1),
(2), (4) Date: Apr. 16, 2013

(87) PCT Pub. No.: WO2012/052891
PCT Pub. Date: Apr. 26, 2012

(65) Prior Publication Data
US 2013/0204299 A1 Aug. 8, 2013

(30) Foreign Application Priority Data
Oct. 22, 2010 (IT) .............................. MO2010A0293

(51) Int. Cl.
*A61F 2/08* (2006.01)
*A61B 17/04* (2006.01)
*A61B 17/00* (2006.01)

(52) U.S. Cl.
CPC ........ *A61B 17/0401* (2013.01); *A61F 2/0811* (2013.01); *A61B 2017/00862* (2013.01);
(Continued)

(58) Field of Classification Search
CPC .. A61B 2017/00862; A61B 2017/0417; A61B 17/0401; A61B 2017/042; A61B 2017/0406; A61B 2017/0414; A61B 2017/0422; A61B 2017/0424; A61B 2017/0425; A61B 2017/0403; A61B 2017/0404; A61B 2017/0408; A61B 2017/0412; A61B 2017/0419; A61B 2017/0427; A61B 2017/0438; A61B 2017/0445; A61B 2017/0446;
(Continued)

(56) References Cited

U.S. PATENT DOCUMENTS 4,997,433 A * 3/1991 Goble .................. A61F 2/0811
606/62
5,372,599 A 11/1994 Martins
(Continued)

FOREIGN PATENT DOCUMENTS

| EP | 1813225 A2 | 8/2007 |
| EP | 1987803 A2 | 11/2008 |
| WO | 9518571 A1 | 7/1995 |

*Primary Examiner* — Darwin P Erezo
*Assistant Examiner* — Katherine H Schwiker
(74) *Attorney, Agent, or Firm* — Pearne & Gordon LLP

(57) ABSTRACT

A fixing device for suture threads to be inserted into a bone tissue comprises: a first portion (11) provided with at least a first eyelet (10), slot or eye, through which at least a first suture thread (4) can be threaded; at least a second portion (12) destined to be coupled stably in a transosseus seating or hole (5) afforded in a cortical part thereof. The second portion (12) is elastically deformable in order to enable effective coupling to the seating or hole (5).

10 Claims, 2 Drawing Sheets

(52) U.S. Cl.
CPC ............... *A61B 2017/0406* (2013.01); *A61B 2017/0414* (2013.01); *A61B 2017/0417* (2013.01); *A61F 2002/0852* (2013.01); *A61F 2002/0882* (2013.01)

(58) Field of Classification Search
CPC ...... A61B 2017/0448; A61B 2017/045; A61B 2017/0451; A61B 2017/0456; A61B 2017/0458; A61B 2017/0459; A61B 2017/0461; A61B 2017/0462; A61F 2002/0852; A61F 2002/0882; A61F 2/0811; A61F 2002/0817; A61F 2002/0841; A61F 2002/0876
USPC ........ 606/139, 148, 232, 233, 300; 132/323, 132/327
See application file for complete search history.

(56) References Cited

U.S. PATENT DOCUMENTS

| | | | |
|---|---|---|---|
| 5,964,764 A * | 10/1999 | West et al. ..................... | 606/232 |
| 6,086,591 A * | 7/2000 | Bojarski .......................... | 606/64 |
| 7,682,374 B2 * | 3/2010 | Foerster et al. .............. | 606/232 |
| 7,695,503 B1 | 4/2010 | Kaiser et al. | |
| 8,109,965 B2 | 2/2012 | Stone et al. | |
| 2002/0007182 A1 * | 1/2002 | Kim ................................ | 606/53 |
| 2003/0105524 A1 * | 6/2003 | Paulos et al. .............. | 623/13.14 |
| 2004/0106847 A1 | 6/2004 | Benderev | |
| 2004/0243179 A1 * | 12/2004 | Foerster ............. | A61B 17/0401 606/232 |
| 2007/0049944 A1 | 3/2007 | Stone et al. | |
| 2008/0161852 A1 | 7/2008 | Kaiser et al. | |
| 2008/0275554 A1 * | 11/2008 | Iannarone et al. ......... | 623/13.14 |
| 2008/0294204 A1 | 11/2008 | Chirico et al. | |
| 2010/0312341 A1 | 12/2010 | Kaiser et al. | |

* cited by examiner

FIXING DEVICE FOR SUTURE THREADS TO BE INSERTED INTO A BONE TISSUE

The present invention relates to a fixing device for suture threads to be inserted into a bone tissue.

Specifically, though not exclusively, it is usefully applied as an instrument for realising surgical operations, aimed at treating lesions which require re-setting and fixing tendons to the respective portions of bone in order to restore the original footprint or for repairing tendon damage.

The emblematic case for use is the suturing of the rotator cuff and, in particular, for the arthroscopic use of transosseus stitches (note: this is true only of systems with a double eyelet).

EP 1987803 shows an expanding plug for tendon fixation which has two resilient arms configured to expand radially to achieve interference fixation of a grat tendon inside of a bone tunnel.

US 2004/0106847 shows a self anchoring slings and deployment mechanism for use therewith in selectively positioning a sling into position within a body US 2008/0161852 features an apparatus and a method for fixing a selected anatomical portion. An anchor may be provided that may be inter connected with a selected graft portion that is operable to pass through a selected bore and then moved into a operable position to engage a selected portion of the bore to eliminate the possibility of the graft moving through the bore.

WO95/18571 shows an anchor and a method for attaching an object to a bone like structure the anchor includes a body and a plurality of barbs which are elastically deformable, axially aligned, circumferentially spaced. The anchor may be pulled along a bone tunnel and has a an opening adapted for connecting an object to itself. The outer ends of the barbs are suitable for fixing the anchor to the bone tunnel.

A limit of the known methods relates to the possibility that the suture may bring about an unloading of forces directly on the bone by the threads, thus producing undesired yielding of the bone tissue which the threads come into contact with.

A further problem encountered in the prior art relates to the difficulty of removal in the event of a further surgical operation.

A further problem of the prior art relates to the difficulty of mounting two or more high-resistance threads, one of which proximal, for the technique that uses transosseus stitches.

A further drawback of note is a limitation in grip, often the reason for the failure of the device.

The aim of the invention is to obviate the above-mentioned drawbacks and problems encountered in the prior art.

Advantages of the invention are the possibility of realising an implant which causes no inflammatory re-absorption reactions, a high level of grip of the system through realising a cortical locking implant and a general simplification of installing the implant.

Further characteristics and advantages of the invention will better emerge from the detailed description that follows of some preferred though not exclusive embodiments of the invention, illustrated by way of non-limiting example in the accompanying figures, in which.

Figure 1:
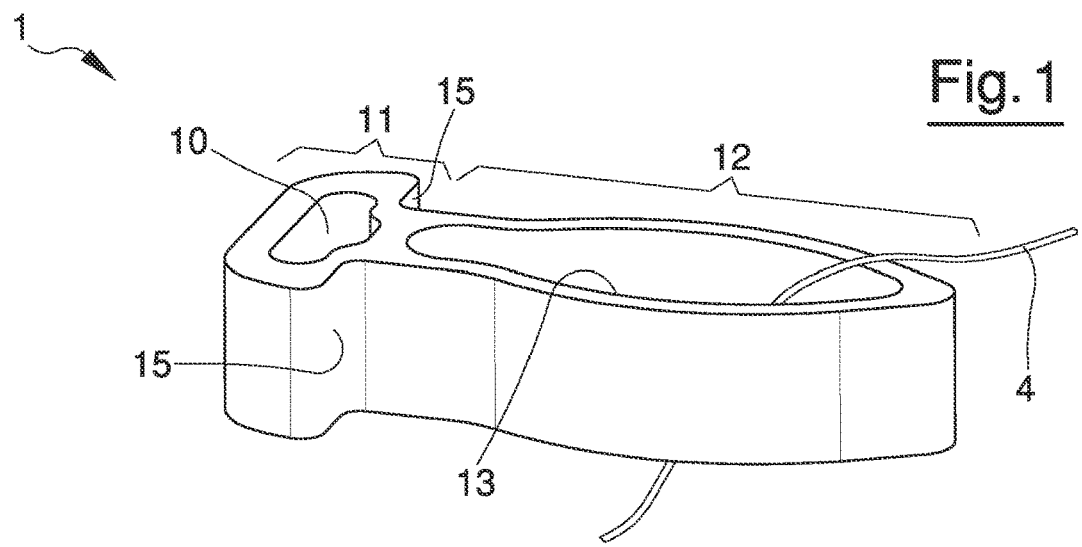
FIG. 1 is a schematic perspective view of a first embodiment.
Figure 2:
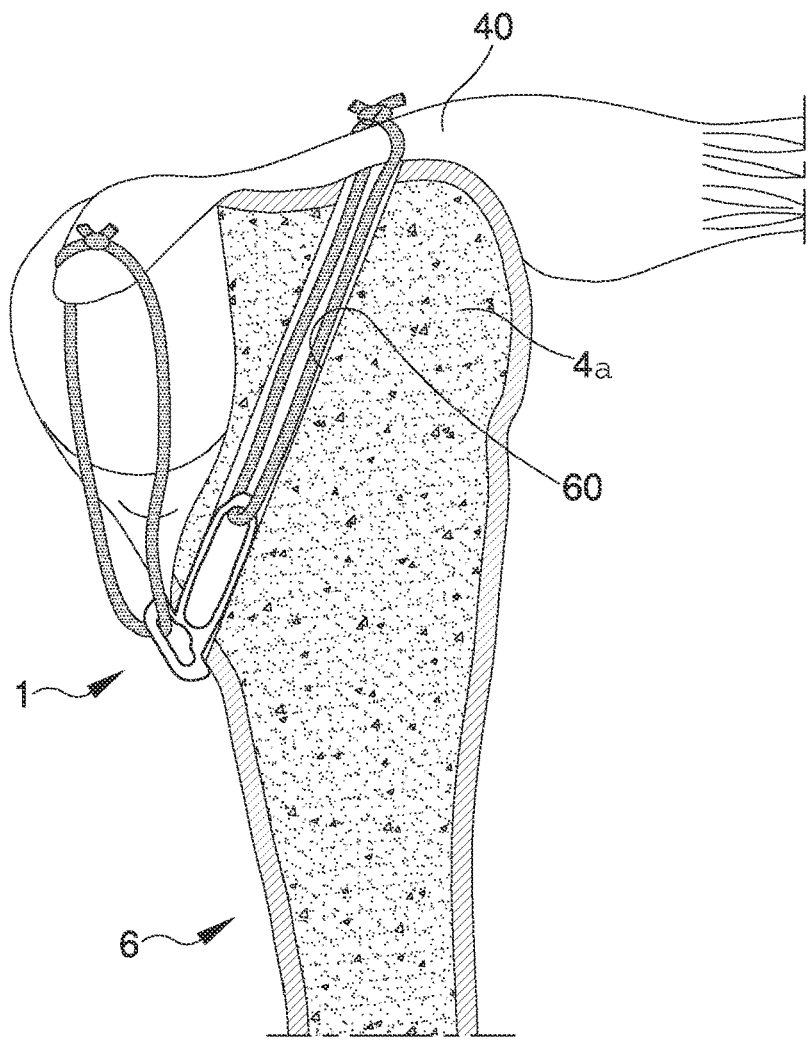
FIG. 2 is a perspective view of an application of the embodiment of FIG. 1.

With reference to the accompanying FIGS. 1 and 2 denote two different embodiments of a fixing device (which can be made of titanium alloy or polyether ether ketone (PEEK)) for suture threads 4 to be inserted in bone tissue.

The fixing devices 1 and 2 respectively comprise: first portions 11 and 21 provided with at least first eyelets (slots or eyes) 10, 20, through each of which at least a suture thread 4 can be passed.

The fixing devices 1, 2 respectively further comprise at least second portions 12, 22 destined to be coupled in a stable and easily removable manner in seatings or holes 5 made in the bone structure, at least in the cortical part thereof.

At least the second portions 12, 22 are furthermore elastically deformable in order to permit an effective coupling to the respective seatings or holes 5. With particular reference to the embodiment illustrated in FIGS. 1 and 2, the corresponding fixing device 1 is constituted by a first portion 11 and a second portion 12 which has an elongate, annular-shaped and hence closed structure, destined to identify a further eyelet, slot or eye 13, through which at least a suture thread 4 can be passed. More specifically, with reference to a median plane of symmetry parallel to the direction of the axis of said further eyelet, slot or eye 13, which identifies the direction of introduction of said suture threads 4, the second portion 12 exhibits overall a convex external conformation in which the opposite central parts of the annular structure thereof project externally relative to the other parts.

The convexity, combined with the elastic deformability of the material, has the function of achieving the solidity of the coupling of the second portion 12 in the corresponding seating or hole 5. The coupling is realised by forcing, in such a manner that once located, by virtue of the elastic return of the second portion 12, the second portion 12 exerts an adequate pressure against the walls of the hole.

The shape of the second portion 12 is such as to allow the suture threads to be tensioned independently without impingement on the bone. The transosseus threads can be brought into different exit positions, thus permitting, together with the external threads, maximization of the footprint.

The independent eyelets make it possible either to tie sutures closed into a loop or to treat the sutures independently.

Further stability of the coupling is provided by the first portion 11 that normally remains at least partly external to the seating or hole 5 due to its mushroom shape, which enables it to rest on the external surface of the bone 6 by means of the parts of surface 15.

FIG. 2 schematically illustrates the final use configuration of the fixing device 1 in the operating technique which includes fixing the tendon by means of internal suture threads 4, i.e. made to pass internally of the bone 6 in a through-channel 60 through the cancellous bone 4a previously realised by the surgeon, and by means of external threads 4.

As can be noted, in the example illustrated in FIG. 2, the fixing of the tendon 40 to the head of the bone (humerus) is made at two points: one using external threads 4 which are fixed in position at the first eyelet 10 of the fixing device 1, the other by means of internal threads 4 which are housed internally of the through-channel 60, made previously, and which are fixed in position at the further eyelet 13 of the fixing device 1.

The situation illustrated enables an immediate understanding of the fact that the forces exerted by the threads are prevented from being unloaded directly onto the bone as the constraining and fixing of the threads is achieved by means of the fixing device or devices 1.

In particular, it can be noted that the fixing device is shaped in such a manner as to realise a favourable distribution of the forces on the bone 6. In fact, the first portion 11 that remains at least partly external to the seating or hole 5, exhibits a mushroom-shaped profile which is suitably orientated, relative to the median longitudinal axis of the fixing device, so as to enable the broadest possible resting contact with the external surface of the bone 6 via the parts of surface 15. In practice, the parts of surface 15, when necessary, as shown in FIG. 2, are inclined relative to the longitudinal median axis of the fixing device by an amount that is sufficient to cause them to adhere to the external (cortical) surface of the bone 6 when the second portion 12 is inserted in the through-channel 60.

Figure 3:
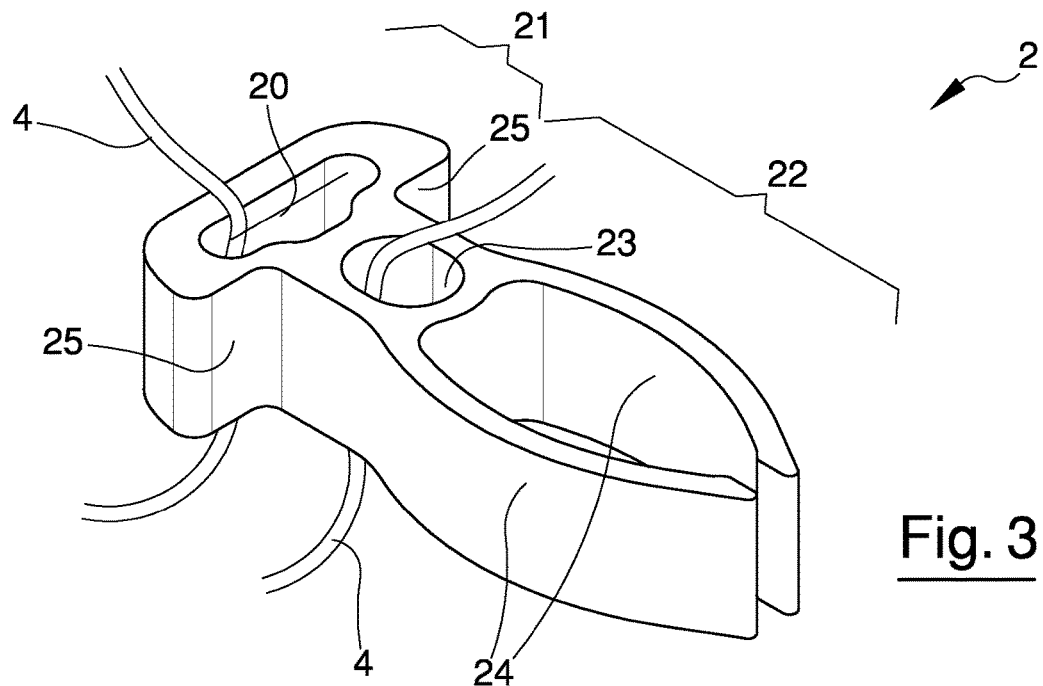
FIG. 3 is a schematic perspective view of a second embodiment.

The fixing device 2, illustrated in FIG. 3, is destined for a similar function; apart from the first portion 21, provided with the first eyelet 20 and with an overall mushroom shape, therefore entirely similar to what is shown for the fixing device 2, again exhibits a second portion 22 with a structure that is elongate, but open and constituted by two branches 24 arranged oppositely relative to a median plane parallel to the directions of the axis of the first eyelet, slot or eye 20, identifying the direction of introduction of the suture threads, and having appropriately rounded ends.

The elongated shape allows the internal sutures to be brought very close to the exit channel, thus minimising the path and facilitating the maintenance of tension in the sutures. The elongate, inclined (following the cortical contact) shape reinforces the pull-out effect.

The shape of the tip allows the resistance of the suture thread to be maintained constant for different pull angles.

The device further exhibits a second eyelet, slot or eye 23, through which at least a suture thread (another thread) can be inserted, different from the thread or threads insertable in the first eyelet 20.

The second eyelet, slot or eye 23 is located between the first eyelet, slot or eye 20 and the second portion 22 constituted by said two branches 24. The presence of the second eyelet 23 has the same aim and performs a function for anchoring the threads 4 like the one performed by the eyelet 13 of the fixing device 1 relative to the first embodiment as previously illustrated.

Figure 4:
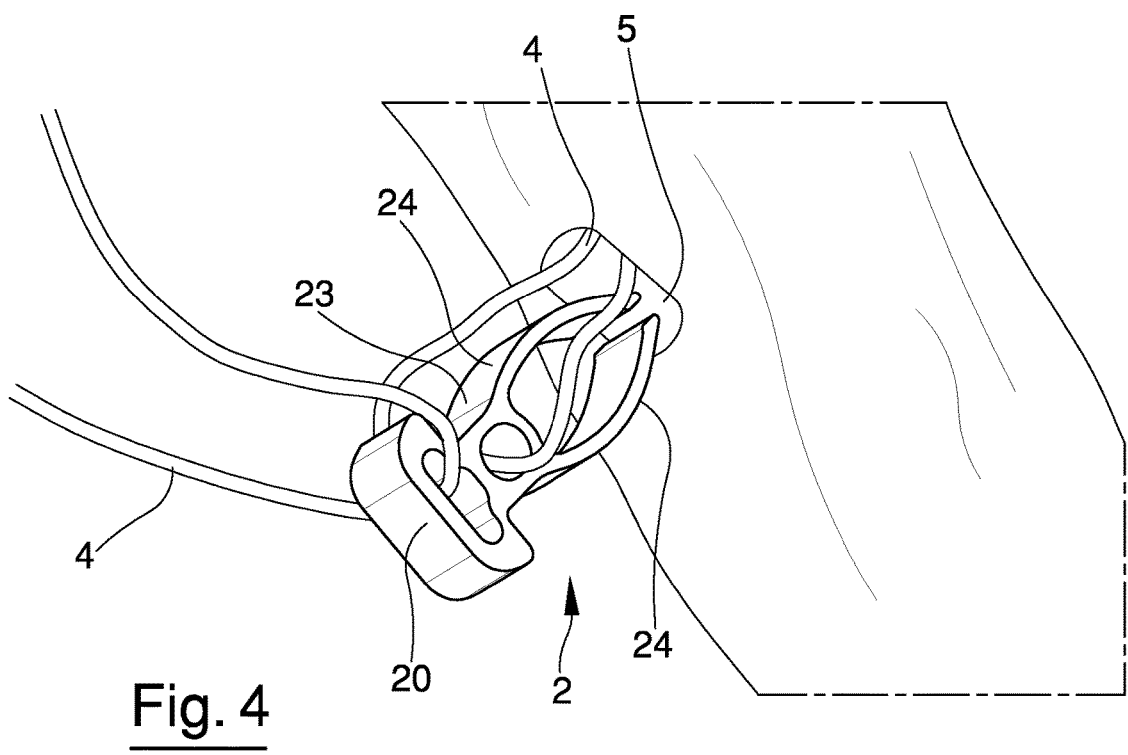
FIG. 4 is a perspective view of an application of the embodiment of FIG. 3.

FIG. 4 schematically illustrates the step of applying the fixing device 2 in the seating or hole 5 previously made in the bone.

In this case, too, the fixing device exhibits a second portion 22 which has the aim of enabling a solid anchorage to the seating or hole 5 made in the bone, just like the second portion 12 of the above-described first embodiment.

The second portion 22, provided with a structure that is elongate, but open and constituted by two branches 24 arranged opposite relative to a median plane, also exhibits overall a convex external conformation in which the opposite central parts of the structure thereof in any case project outwardly relative to the other parts.

In this case, too, the convexity, combined with the elastic deformability of the material, has the function of enabling the solidity of the coupling of the second portion 22 in the corresponding seating or hole 5. The coupling is in fact realised forcibly in such a manner that once located, thanks to the elastic return of the branches 24 of the second portion 22, an adequate pressure is exerted against the walls of the hole, which produces a stable adhesion of the branches and thus overall of the second portion to the walls of the seating or hole 5. Further stability is given to the coupling by the first portion 21 that normally remains at least partly external to the seating or hole 5 by virtue of the mushroom-shaped profile thereof, which enables it to rest on the external surface of the bone 6 by means of the parts of surface 25.

The zones 15 and 25 guarantee a cortical hold.

Obviously, the dimensions of the seating or hole 5, in this embodiment as well, must be suitably proportioned to the dimensions of the second portion of the fixing device so that the necessary forcing is realised in the coupling.

In this embodiment, too, the mushroom-shaped profile of the first portion 21 is appropriately orientated relative to the median longitudinal axis of the fixing device in such a way as to enable the broadest possible resting contact with the external surface of the bone 6 by means of the parts of surface 15. This means that the parts of surface 25, when required, are inclined relative to the median longitudinal axis of the fixing device by the amount necessary to make them fully adhere to the external surface of the bone when the second portion 22 is inserted in the hole 5.

In general, the use of the fixing devices according to the invention is excellent for performing external and transosseus stitches during suture operations such as that on the rotator cuff and the like.

By acting on the geometry and thickness of the various parts of the device it is possible to obtain significant variants of rigidity which allow the device to be inserted into bone of greatly differing quality (e.g. osteoporotic bone or bone of good quality).

Thanks to the structure and conformation thereof, the invention further prevents suture threads from unloading the forces directly on the bone, thus avoiding yielding of the bone and increasing overall the hold and reliability of the whole lesion repair system.

The invention claimed is:

1. A fixing device for suture threads to be inserted into a bone structure, comprising a first portion (11, 21) and a second portion (12, 22), the device having an undeployed state, a deployed state, and a longitudinal dimension, the deployed state being a state when the device is deployed in a bone structure, the first portion (11, 21) being provided with a first eyelet (10, 20) or eye effectively sized to receive a first suture thread (4) therethrough, the first eyelet or eye defining an opening which extends through the device in a direction substantially perpendicular to the longitudinal dimension in the undeployed state, the second portion (12, 22) exhibiting a second eyelet or eye effectively sized to receive a second suture thread (4) therethrough, the second portion (12, 22) comprising an engagement portion which is effectively sized and shaped such that it can effectively contact and engage an interior surface of a transosseus seating or hole (5) afforded in the bone structure to thereby stably couple the device with the bone structure, the second portion (12, 22) having a neck portion located between the engagement portion and the first portion, the engagement portion being spaced apart from the first portion, the engagement portion having a medial portion and a distal portion, the medial portion being located between the neck portion and the distal portion, the device being configured so that, in use, the engagement portion is inserted, distal portion first, into the transosseus seating or hole (5), the neck portion having a first width transverse to the longitudinal dimension, the first portion comprising a mushroom-shaped portion having a second width transverse to the longitudinal dimension, the second width being larger than the first width in both the undeployed state and the deployed state, the second width being larger than the first width when the first eyelet or eye defines the opening in the undeployed state, the mushroom-shaped portion being integral with the neck portion, the neck portion being integral with the engagement portion, the mushroom-shaped portion extending beyond the neck portion in a first direction transverse to the longitudinal dimension in both the undeployed state and the deployed state, the mushroom-shaped portion extending beyond the neck portion in a second direction transverse to the longitudinal dimension in both the undeployed state and the deployed state, the second direction being opposite to the first direction, and wherein at least the second portion (12, 22) is elastically deformable in order to enable effective coupling to the transosseus seating or hole (5).

2. The device of claim 1, characterised in that the send portion (12) has an annular and therefore closed elongate structure, effective to identify the second eyelet or eye, through which the second suture thread (4) can be threaded.

3. The device of claim 2, characterised in that the second portion (12) exhibits overall a convex external conformation in which opposite central parts of the annular structure are projecting externally relative to other parts thereof.

4. The device of claim 1, characterised in that the second portion (22) has an open elongate structure comprising two opposite branches (24).

5. The device of claim 4, characterised in that the second portion (22) comprises the second eyelet (23) or eye, through which the second suture thread (4) can be threaded, located between the first eyelet (20) or eye and the two opposite branches (24).

6. The device of claim 4, characterised in that the two branches (24) together give rise to a convex external conformation in which opposite central parts of the two branches (24) are convex and projecting externally relative to other parts of the device.

7. The device of claim 6, characterised in that in use the first portion (11, 21) remains at least partly external to the seating or hole (5) due to the mushroom-shaped portion, which enables the mushroom-shaped portion to rest on the external surface of the bone structure (6), and the mushroom shaped portion is orientated relative to a median longitudinal axis of the device so as to enable an effective resting contact with the external surface of the bone structure (6) via parts of a resting surface (15, 25).

8. The device of claim 1, characterised in that, during application, at the first eyelet (10, 20) of the device (1) and at the second eyelet (13, 23) there are fixed in position external suture threads (4), effective to pass internally of the bone structure (6) in a through-channel (60) previously formed by a surgeon.

9. The device of claim 1, characterised in that the device is made of titanium alloy or PEEK.

10. The device of claim 1, wherein the first suture thread (4) extends through the first eyelet (10, 20) or eye, and wherein the second suture thread (4) extends through the second eyelet or eye.

* * * * *